United States Patent [19]

Rehder

[11] 4,246,895

[45] Jan. 27, 1981

[54] APPARATUS FOR PRODUCING A CONICAL SURFACE ON A BONE

[76] Inventor: Günther Rehder, Mümmelmannstrasse 10, 2805 Stuhr 3, Fed. Rep. of Germany

[21] Appl. No.: 42,807

[22] Filed: May 29, 1979

[30] Foreign Application Priority Data

Aug. 4, 1978 [DE] Fed. Rep. of Germany ....... 2834295

[51] Int. Cl.³ .................. A61F 5/04; A61F 17/32; B26B 7/00
[52] U.S. Cl. .................. 128/92 E; 30/276; 128/305
[58] Field of Search ............ 128/321, 305, 305.1, 128/304, 310, 312, 317, 92 C, 92 CA, 92 BA, 92 E, 92 EB, 92 EA; 30/276, 300, 310; 175/286, 289

[56] References Cited

U.S. PATENT DOCUMENTS

| 1,002,242 | 0/1911 | Ehrhardt | 30/276 |
| 1,408,275 | 0/1922 | Eckles | 128/92 E |

*Primary Examiner*—Robert W. Michell
*Assistant Examiner*—C. W. Shedd

[57] ABSTRACT

An apparatus for producing a conical, outwardly tapering surface on a bone, especially on a cylindrically preworked femur head of a human hip joint. The apparatus includes a drive shaft having a free end. A knife-type cutting device is arranged at the free end of the drive shaft, wherein the cutting device has an inner edge. An adjusting device is included for moving the inner cutting edge of the cutting device from an initial position essentially parallel to the longitudinal axis of the drive shaft to a position forming an acute angle relative to the longitudinal axis. The cutting edge of the cutting device is radially outwardly offset relative to the longitudinal axis of the drive shaft. In the initial position, the extent of radial offsetting is at least as great as half the diameter(r) of the bone section to be treated.

18 Claims, 2 Drawing Figures

4,246,895

APPARATUS FOR PRODUCING A CONICAL SURFACE ON A BONE

FIELD OF THE INVENTION

The invention relates to an apparatus for producing a conical surface which tapers from the outside, on a bone, especially on a cylindrically pre-worked femur head of a human hip joint.

BACKGROUND OF THE INVENTION

When endoprostheses are implanted, especially shell-shaped prostheses or parts of prostheses, respectively, it is necessary, especially in hip joints, for creating suitable fitting areas, to prepare the existing natural shape of the bone section by a chip-removing process. This is done so that the bone or bone section, respectively, which is provided with the prosthesis or the part of the prosthesis, is geometrically adapted to the shape of the prosthesis or the part of the prosthesis.

To attach a shell prosthesis on the femur head of a hip joint, first it is necessary to provide a cut, which is usually circular, on the front side of the femur head, which cut is adapted to the inner side of the prosthesis.

Afterwards, the femur head has to be worked at its outer side, which is adjacent to the front side, in order to create a suitable fitting area for the jacket of the shell prosthesis.

For shell prostheses which are known per se, it is sufficient when the above-mentioned outer side of the bone is cylindrically cut. However, to improve these known shell prostheses having cylindrical jackets, there have been developed shell prostheses whose jacket surfaces are not cylindrical, but conically tapered towards the free edge. Accordingly, for mounting such a shell prosthesis, it is necessary to provide a conical area which tapers from the outside on the bone or bone section to be treated. In the case of a human hip joint, this is the femur head which can be pre-worked cylindrically.

Such a treatment obviously results in considerable problems because the fitting areas, which had been created in advance, may not be damaged during this treatment. Moreover, the basic principle has always to be adhered to that only as little tissue as possible should be removed in order to reduce the extent or seriousness of the operation and not to lose the advantages which are achieved with shell-shaped prostheses as compared to total-endoprostheses.

A primary object of the present invention is to create an apparatus of the type described with which a conical area which tapers from the outside, is produced on a bone or bone section, especially the femur head of a human hip joint, without damaging the rounded fitting area (usually prepared in advance) on the front side of the bone. The conical area which is to be produced must reliably be axis symmetrical in order to guarantee an optimum adaptation to the geometric form of the existing shell prosthesis and, thus, to use only as little amount of bone cement as possible. Removal of portions of tissue, whose removal is not necessary, must be avoided. Further, it should be possible to treat the bone as quickly as possible, in order to keep the time of the operation as short as possible.

SUMMARY OF THE INVENTION

According to the invention, a solution of this object resides in the provision of an apparatus which is characterized by a drive shaft at whose free end there is arranged a knife-type cutting means. The cutting means has an inner cutting edge which is radially outwardly offset to the longitudinal axis of the drive shaft, and which, by means of an adjusting device must be moved from an essentially parallel initial position to a position forming an acute angle relative to the longitudinal axis. The extent of the radial offsetting of the cutting edge in the initial position (and, preferably, also in the end position) is at least as great as half the diameter of the bone section which is to be treated.

In a preferred further development of the present invention, the knife-type cutting means is mounted in an articulated manner on a supporting body which is arranged on the lower end section of the drive shaft. In this arrangement, the adjusting device acts on the end section of the cutting means which is provided above the hinge point.

For a better understanding of the present invention, reference is made to the following description and accompanying drawings, while the scope of the present invention will be pointed out in the appended claims.

DESCRIPTION OF THE PREFERRED EMBODIMENTS

Figure 1:
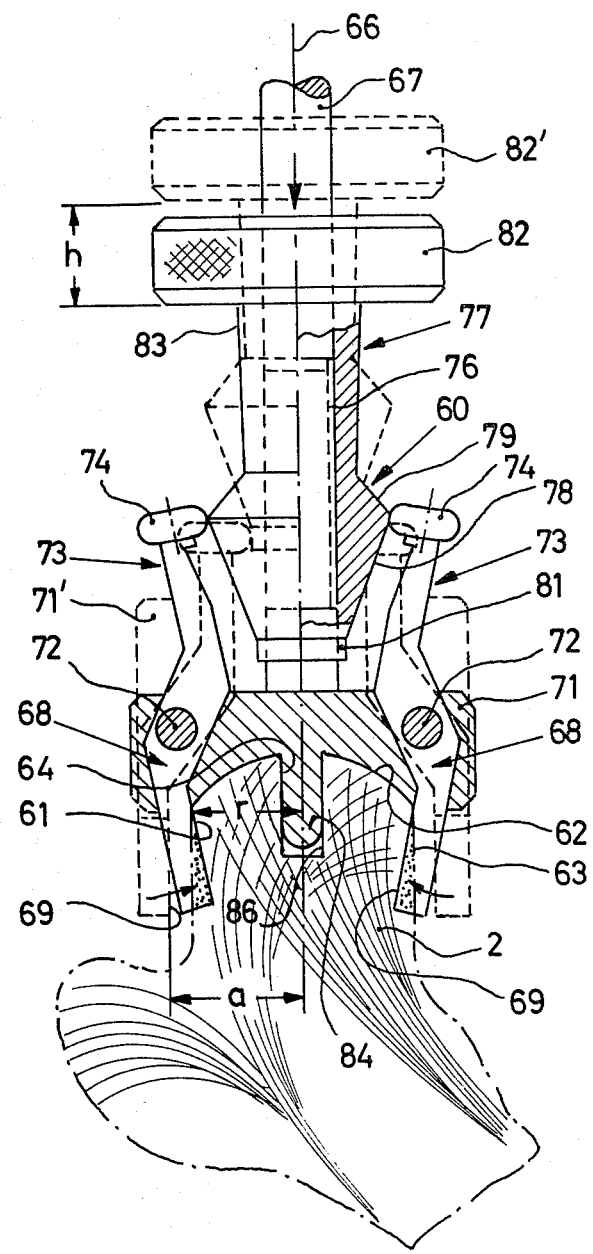
FIG. 1 shows a lateral top view of an arrangement according to the invention, partially in sectional view, wherein the final stage of the treatment is shown in solid lines.

FIG. 1 of the drawings shows, in solid lines, an apparatus 60 for producing a conical surface 61 on a bone or bone section 2, respectively, which, in this case, is the femur head of a human hip joint.

Before using the apparatus 60, the femur head 2 has already been preliminarily worked by means of a suitable device, i.e., the head has on its front side a circularly rounded surface 62 and on its section, which is adjacent to the front side 62, a cylindrical area 63, as shown in FIG. 1 with dash-dotted lines.

Moreover, concentrically to the femur head 2, a blind end bore 64 with a diameter of 8 mm had been made by means of a shank cutter or twist drill, preferably guided by a Kirschner wire.

The apparatus 60 has a drive shaft 67 which can be driven about its longitudinal axis 66 and on whose free end there are arranged two knife-type cutting means 68 whose radially inwardly arranged cutting edges 69 are moved by an adjusting device, from an essentially parallel initial position, which is radially offset outwardly to the longitudinal axis 66, to a position forming an acute angle relative to the longitudinal axis 66. The extent of the radial offsetting a of the cutting edges 69, in the initial position, is at least the same size as and, preferably, a little larger than half the diameter r of the bone section 2 which is to be treated. This adjusting device is subsequently described in detail.

Since the two knife-type cutting means 68, which are arranged diametrically opposed to each other and mirror-symmetrically with respect to the longitudinal axis 66, do not differ in principle from each other, only one of the cutting means 68 will be described.

The cutting means 68 is attached in an articulated manner to a pot-shaped supporting body 71 which is arranged on the lower end section of the drive shaft 67 in such a manner that the adjusting device, which is to be described, can act on the end section 73 of the cutting means 68 arranged above the hinge 72. The attachment to the disk-shaped or pot-shaped supporting body 71 is accomplished by joint bolts, wherein the supporting body 71 is provided with respective recesses in which the cutting means 68 are arranged.

On the guiding end of the cutting means 68, there is an outer guide body 74 which is circularly constructed and which is rotationally movably and axially immovably supported by a roller bearing on the upper end of portion 73.

The guide body 74 cooperates with the adjusting device which is described in the following.

The adjusting device consists, essentially, of an adjusting bash 77 which is arranged concentrically to the drive shaft 67 by means of a fine thread 76. The outer diameter of the adjusting bush 77 increases continually from its lower end through a first axial longitudinal portion 78 which is conically constructed and, then, diminishes again through a following second axial longitudinal portion 79 which is also conically constructed.

The lowest end section 81 of the adjusting bush 77 is cylindrically formed and has a diameter which is of such size that the cutting means 68 assumes an essentially parallel position when its upper guide end, which faces away from the cutting edge 69, i.e., its guide body 74, fits on the lowest end section 81 of the adjusting bush 77. This condition is shown in FIG. 1 with dotted lines; however, in FIG. 1, the supporting body 71 with its cutting means 68, is not in the initial position, which is further up, but in the final position of the treatment, for clarity. This is, however, insignificant with respect to the position of the cutting means 68 relative to the longitudinal axis 66.

The diameter of the adjusting bush 77 on the upper end of the second axial longitudinal portion 79, or directly behind it, respectively, is of such size that the smallest distance of the cutting means 68 to the longitudinal axis 66 is larger than the largest radius r of the femur head 2 which is to be treated or was treated.

Between the second axial longitudinal section 79 of the adjusting bush 77 and its end constructed as adjusting flange 82, there is arranged a section 83 which—slightly conically—ascends upwardly.

The jacket surface of the adjusting flange 82 is roughened by edging or beading.

The supporting body 71, which is pot-shaped and is open outwardly and whose inner front side corresponds with the form of the inner side of the prosthesis shell which is to be applied, is provided with a centering pin 84 which protrudes downwardly.

The manner of operation of the apparatus, according to the invention, is as follows:

At the beginning of the treatment, the position of the adjusting bush 77 relative to the drive shaft 67 is such that the guide bodies 74 of the knife-type cutting means 68 rest on the lowest end section 81 of the adjusting bush 77 which is cylindrically formed, as shown in FIG. 1 in dash-dotted lines. The adjusting flange 82 is arranged in the initial position, and is identified in FIG. 1 by 82', so that, in contrast to the simplified representation according to FIG. 1, the supporting body 71 is also actually shown in a higher position for reasons of clarity and is identified by 71'. Thus, the cutting means 68 are also arranged in a higher position by about a distance h, than is shown in FIG. 1. On the other hand, their position relative to the longitudinal axis 66 coincides with the positions shown, which is very important. That is, the cutting edges 69 are nearly parallel to the longitudinal axis 66, each radially offset by about a distance a.

In this position, the centering pin 84 is then inserted in the already mentioned central bore 86, wherein the hand of the operating surgeon holds the apparatus 60 on the drive shaft 67 (and not yet on the adjusting flange 82).

When the hand of the operating surgeon acts on the adjusting flange 82, there is accomplished a downwardly, radially directed adjustment of the adjusting bush 77, as a result of the fine thread 76 which is constructed as a left-hand thread and which connects the drive shaft 67 with the adjusting bush 77. Thus, the guide bodies 74 start to move upwardly along the conically-constructed, first axial longitudinal portion 78 of the adjusting bush 77. The upper end sections 73 of the cutting means 68 are, therefore, tilted about the hinge 72 outwardly and, accordingly, the lower lever section of the cutting means 68 (which include the cutting edges 69) are tilted inwardly. This leads to an engagement of the upper end sections 73 with the cylindrical surface 63 of the femur head 2 and, therefore, they start to remove the tissue shown in FIG. 1 in dotted lines, i.e., the tissue between the cylindrical area 63 and the conical area 61 of the femur head 2.

When the guide bodies 74 have reached the upper end of the conical first axial longitudinal portion 78 of the adjusting bush 77, as shown in FIG. 1 with solid lines, the production of the conical surface on the femur head 2 is ended; the surface tapers from the outside or widens outwardly.

The apparatus 60, however, can obviously not be moved upwardly, because, otherwise, the cutting edges 69 would, then, obviously damage the tissue of the femur head 2 which is to be treated.

One possibility for removing would be to stop the actuation of the drive shaft 67 and to upwardly screw the adjusting bush 77 in a direction reverse to that of the drive drive shaft 67. However, this would be relatively time-consuming.

With the apparatus according to the invention, the releasing of the cutting means 68 is accomplished automatically, because the guide bodies 74 now operate, with further holding of the adjusting bush 77 on the adjusting flange 82 and the still operating drive shaft 67, over the second axial longitudinal section 79, which is conically constructed in the opposite direction. The cutting means 68, again, are swivelled around their hinge 72, until the guide bodies 74 have reached the lower end section of the section 83 of the adjusting bush 77, i.e., a position in which the cutting edges 69 are, again, arranged almost parallel to the longitudinal axis 66 and, in any case, are swivelled outwardly a sufficient distance so that the apparatus 60 can be moved upwardly without engaging the cutting edges 69 with the femur head 2.

Figure 2:
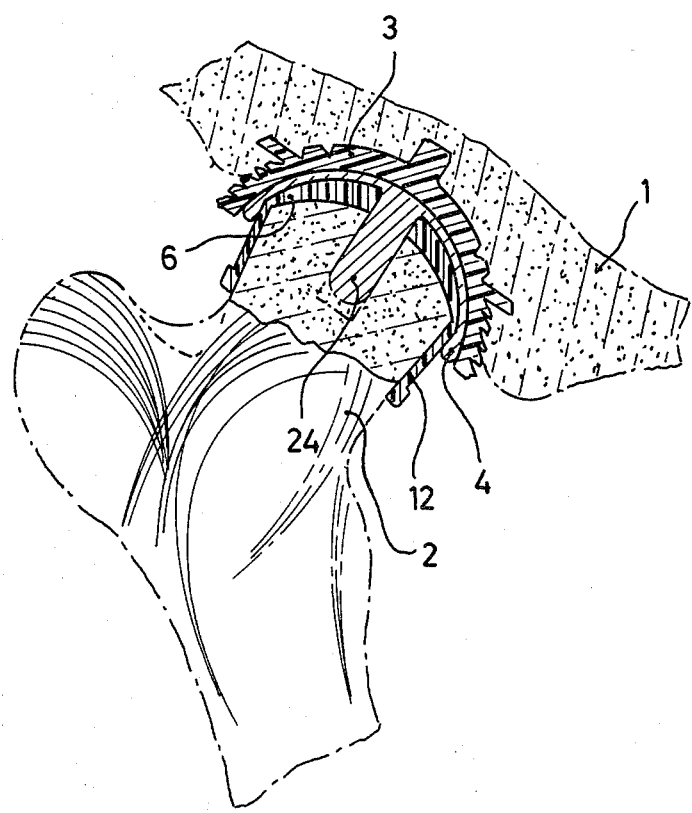
FIG. 2 shows the bone which was treated with the apparatus according to FIG. 1, after insertion of the shell implant.

FIG. 2 of the drawing, shows an embodiment wherein a bone which has been treated in the described way, is provided with a shell prosthesis. The shell prosthesis for the femur head 2 consists in the present case of a double shell, including an inner femur head shell 6 of plastic and an outer femur head shell 4 of metal. A guide pin 24 of the outer femur head shell 4 projects through a respective bore into the inner femur head shell 6 and extends into the bore 86 of the femur head 2.

The curvature of the inner femur head shell 6 on its inside is equal to the curvature of the rounded area 62 on the front side of the femur head 2 and, therefore, is also equal to the curvature on the inner front side of the supporting body 71.

It can be seen that the inner femur head shell 6 has a jacket 12 which runs corresponding to the conical area 61 created at the femur head 2 by means of the apparatus 60 and, therefore, guarantees an exceptional holding action. The possibility of attaching the inner femur head shell 6 to the femur head 2, created in this manner, is guaranteed by sufficient elasticity which, inter alia, can be created by a radial slot which does not negatively influence the positive locking after attachment.

For the sake of completeness, it shall be mentioned that in the Acetabulum 1 there is arranged, as countersliding surface for the outer femur head shell 4, an Acetabulum pan 3 of plastic.

As described above, various features of the invention are most advantageous. In this regard, the adjusting device has, preferably, an adjusting bush which is arranged concentrically to the drive shaft and is axially movable relative to this drive shaft, wherein the outer diameter of the adjusting bush increases from its lower end section to a first axial longitudinal portion and diminishes to an adjacent second longitudinal portion, both axial longitudinal portions, preferably, being constructed conically.

The lowest end section of the adjusting bush can have a diameter of such a size that the cutting means or, more exactly, that section which is provided with the cutting edge, assumes an essentially parallel position (initial position), when the upper guide end of the cutting means, which faces away from the cutting section, fits on the lowest end section of the adjusting bush. In this manner, first, the apparatus is attached to the bone without damaging the bone.

In order to be able to remove the apparatus, after finished treatment, without further damaging the bone, the diameter of the adjusting bush is on the upper end of the second axial longitudinal section, preferably, having such a size that the smallest distance of the cutting means to the longitudinal axis is larger than the largest radius of the bone section to be treated.

It is especially suitable when the apparatus has two cutting means which are located opposite each other, preferably diametrically opposite each other. In this manner, not only is a quicker treatment achieved but, also, a state of equilibrium of the forces during treatment is obtained.

For adjusting the cutting means during the treatment, the adjusting bush, preferably, engages the drive shaft by means of a fine thread, i.e., a thread with smaller thread pitch. It is, furthermore, preferred that the thread pitch is oppositely directed to the rotational direction of the drive shaft.

Furthermore, the adjusting bush can be provided at its upper end section with an adjusting flange or the like, by means of which the adjustment is ultimately effected during the treatment.

The supporting body is provided, in one embodiment, on its outer side with a centering pin which protrudes downwardly and which is otherwise suitably constructed in a pot-shape, i.e., partially hollowed form wherein the shape of its inner front side, directed outwardly, is suitably constructed in the shape of the inner side of the shell prosthesis which is to be attached, or of the outer side of the bone which is suitably already prepared.

It can be seen that, with the apparatus 60 according to the invention, there can be made, in quick and safe manner, a tapered conical surface on the bone from without which surface is exactly axis symmetrical, so that, after treatment, there can be achieved extraordinarily exact fitting surfaces which are the prerequisite for a physiologically correct construction of the implant.

Because of the automatic ending of the cutting process and of the centering of the apparatus, there is no removal of tissue which does not have to be removed per se, as is the case when there is free exposed treatment. The operating surgeon can do the adjusting extremely sensitively and can interrupt it at any time, which is accomplished by releasing an adjusting flange. In spite of these numerous advantages which include, in addition, a very short operation time, the apparatus according to the invention is extremely simply constructed and, therefore, is very inexpensive. Finally, it can be extremely simply disassembled into its individual parts when the apparatus must be cleaned.

While the foregoing description and drawings represent the preferred embodiments of the present invention, it will be obvious to those skilled in the art that various changes and modifications may be made therein without departing from the true spirit and scope of the present invention.

| LIST OF REFERENCE NUMERALS | |
|---|---|
| 1 | Acetabulum |
| 2 | Femur head |
| 3 | Acetabulum pan |
| 4 | Outer femur head shell |
| 6 | Inner femur head shell |
| 12 | Jacket (of 6) |
| 24 | Guiding pin (of 4) |
| 60 | Apparatus |
| 61 | Conical surface (of 2) |
| 62 | Sounded surface (of 2) |
| 63 | Cylindrical surface (of 2) |
| 64 | Blind-end bore (in 2) |
| 66 | Longitudinal axis (of 67) |
| 67 | Drive shaft |
| 68 | Knife-type cutting means |
| 69 | Cutting edges (of 68) |
| 71, 71' | Supporting body |
| 72 | Hinge point (from 68 to 71) |
| 73 | Upper end section (of 68) |
| 74 | Guide body (to 73) |
| 76 | Fine thread |
| 77 | Adjusting bush |
| 78 | First axial longitudinal section (of 77) |
| 79 | Second axial longitudinal section (of 77) |
| 81 | Lower end section (of 77) |
| 82, 82' | Adjusting flange |
| 83 | Section (of 77) |
| 84 | Centering pin (of 71) |
| 86 | Central bore (in 2; for 84) |

What is claimed is:

1. An apparatus for producing a conical, outwardly tapering surface on a bone, especially on a cylindrically-worked femur head of a human hip joint, comprising:
   a drive shaft, said drive shaft having a free end and a longitudinal axis;
   a knife-type cutting means being arranged at said free end of the drive shaft, said cutting means having an inner edge; and adjusting means for moving said inner cutting edge of said cutting means from an initial position essentially parallel to the longitudinal axis of the drive shaft, the cutting edge being radially outwardly offset relative to the longitudinal axis of the drive shaft, to a position forming an acute angle relative to the longitudinal axis;

wherein, in the initial position, the extent of radial offsetting is at least as great as half the diameter (r) of the bone section to be treated.

2. An apparatus according to claim 1, including a supporting body, and wherein the knife-type cutting means is mounted in a hinged manner to said supporting body which is arranged on the lower end section of said drive shaft, said adjusting device acting on end sections of said cutting means provided above the hinge point.

3. An apparatus according to claim 2, wherein said supporting body is constructed in a disk-shaped manner.

4. An apparatus according to claim 2, wherein said supporting body is provided with a centering pin protruding downwardly.

5. An apparatus according to claim 2, wherein said supporting body is constructed in a pot shape and is outwardly open, wherein the shape of its inner front side corresponds to the shape of the inner side of the shell prosthesis which is to be applied.

6. An apparatus according to claim 1, wherein said adjusting means includes an adjusting bush which is arranged concentrically to the drive shaft and is axially movable relative to the drive shaft, the outer diameter of said adjusting bush increasing from the lowest end section to a first axial longitudinal portion and diminishing to an adjacent second axial longitudinal portion.

7. An apparatus according to claim 6, wherein said first axial longitudinal section of said adjusting bush is constructed conically.

8. An apparatus according to claim 6, wherein said second axial longitudinal section of the adjusting bush is constructed conically.

9. An apparatus according to claim 6, wherein the lowest end section of said adjusting bush includes a diameter of such a size that the cutting means assumes an essentially parallel position, when its upper guide end which is faced away from the cutting edge, fits on the lowest end section of said adjusting bush.

10. An apparatus according to claim 9, wherein said adjusting bush has on its upper end section an adjusting flange.

11. An apparatus according to claim 10, wherein said adjusting flange is roughened on its jacket by knurling.

12. An apparatus according to claim 6, wherein the diameter of said adjusting bush on the upper end of said second axial longitudinal section is of a size such that the smallest distance of the cutting edge to the longitudinal axis is larger than the largest radius r of the bone section to be treated.

13. An apparatus according to claim 6, wherein the guiding end of said cutting means includes an outer guide body which is rotationally movably but axially immovably supported on the upper end of said guide means.

14. An apparatus according to claim 13, wherein said guide body is supported at the upper end of said guide means by means of a ball bearing.

15. An apparatus according to claim 1, wherein two cutting means are provided diametrically opposite to each other.

16. An apparatus according to claim 1, wherein said adjusting bush is connected to said drive shaft by means of a thread.

17. An apparatus according to claim 16, wherein said thread is a fine thread with small pitch.

18. An apparatus according to claim 16, wherein said thread pitch is oppositely directed to the rotational direction of said drive shaft.

* * * * *

UNITED STATES PATENT OFFICE
CERTIFICATE OF CORRECTION

Patent No. 4,246,895  Dated January 27, 1981

Inventor(s) GÜNTHER REHDER

It is certified that error appears in the above-identified patent and that said Letters Patent are hereby corrected as shown below:

In the heading of the patent [73] should read as follows:

[73]  Assignee:
ORTHOPLANT ORTHOPÄDISCHE IMPLANTE GmbH & Co. KG
Bremen, Germany

Signed and Sealed this

Third Day of November 1981

[SEAL]

Attest:

GERALD J. MOSSINGHOFF

Attesting Officer

Commissioner of Patents and Trademarks